US012558230B2

(12) United States Patent
Lee et al.

(10) Patent No.: US 12,558,230 B2
(45) Date of Patent: Feb. 24, 2026

(54) INTERBODY FUSION DEVICE

(71) Applicant: CG MedTech Co., Ltd., Gyeonggi-do (KR)

(72) Inventors: Suk-Woo Lee, Seoul (KR); Sung-Chul Hwang, Gyeonggi-do (KR); Jun-Taek Lim, Gyeonggi-do (KR)

(73) Assignee: CG MedTech Co., Ltd., Gyeonggi-do (KR)

( * ) Notice: Subject to any disclaimer, the term of this patent is extended or adjusted under 35 U.S.C. 154(b) by 124 days.

(21) Appl. No.: 18/138,974

(22) Filed: Apr. 25, 2023

(65) Prior Publication Data

US 2023/0355404 A1 Nov. 9, 2023

(30) Foreign Application Priority Data

May 3, 2022 (KR) ........................ 10-2022-0054779

(51) Int. Cl.
*A61F 2/44* (2006.01)
*A61F 2/46* (2006.01)
(52) U.S. Cl.
CPC .......... *A61F 2/4455* (2013.01); *A61F 2/4611* (2013.01)
(58) Field of Classification Search
CPC ...... A61F 2/4455; A61F 2/447; A61F 2/4611; A61F 2/442; A61F 2002/4495
See application file for complete search history.

(56) References Cited

U.S. PATENT DOCUMENTS

| | | | |
|---|---|---|---|
| 8,454,666 B2 * | 6/2013 | Tornier .............. | A61B 17/8042 606/71 |
| 9,055,983 B1 * | 6/2015 | Radcliffe ........... | A61B 17/8033 |
| 9,924,984 B2 * | 3/2018 | Hartdegen ......... | A61B 17/8863 |
| 11,766,339 B1 * | 9/2023 | Schifano ............. | A61F 2/30771 623/17.11 |
| 2010/0121383 A1 * | 5/2010 | Stanaford .......... | A61B 17/8042 606/280 |
| 2012/0191141 A1 * | 7/2012 | Costabile ........... | A61B 17/8047 606/295 |
| 2014/0277456 A1 * | 9/2014 | Kirschman ............. | A61F 2/447 623/17.11 |
| 2015/0100094 A1 * | 4/2015 | Milz .................... | A61B 17/808 606/280 |
| 2016/0151166 A1 | 6/2016 | Morris et al. | |
| 2018/0296348 A1 * | 10/2018 | Ryu .................... | A61B 17/686 |

FOREIGN PATENT DOCUMENTS

| | | |
|---|---|---|
| JP | 2017-501002 | 1/2017 |
| KR | 10-2015-0000249 | 1/2015 |
| KR | 10-2122716 | 6/2020 |
| KR | 10-2022-0042777 | 4/2022 |

* cited by examiner

*Primary Examiner* — Eduardo C Robert
*Assistant Examiner* — Holly Joanna Lane
(74) *Attorney, Agent, or Firm* — Wells St. John P.S.

(57) ABSTRACT

Proposed is an interbody fusion device including a circular opening into which a fixator can be inserted, an elastic band configured to surround at least a portion of the circular opening, and comprising a first distal end including a fixing part protruding from the circular opening to prevent separation of the fixator, and a connection part connected to a second distal end of the elastic band, the elastic band is implemented with the same material as the interbody fusion device, and the elastic band and the interbody fusion device are integral.

7 Claims, 9 Drawing Sheets

【FIG. 1】
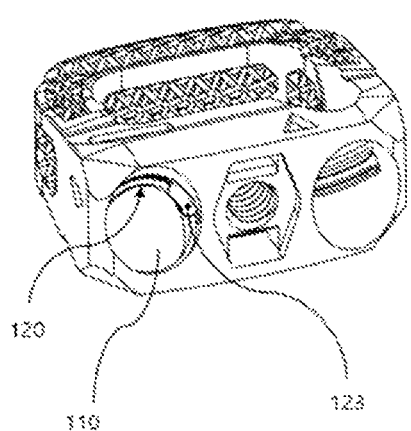

【FIG. 2】
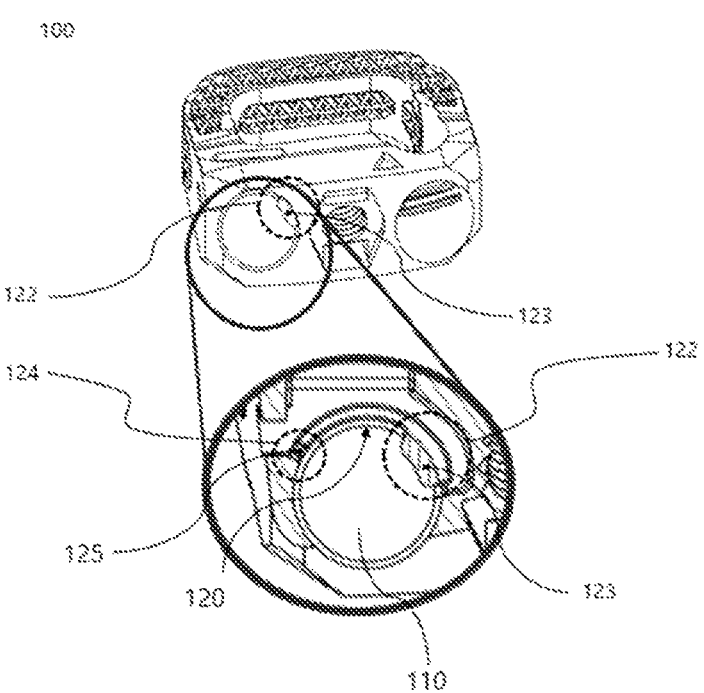

【FIG. 3A】
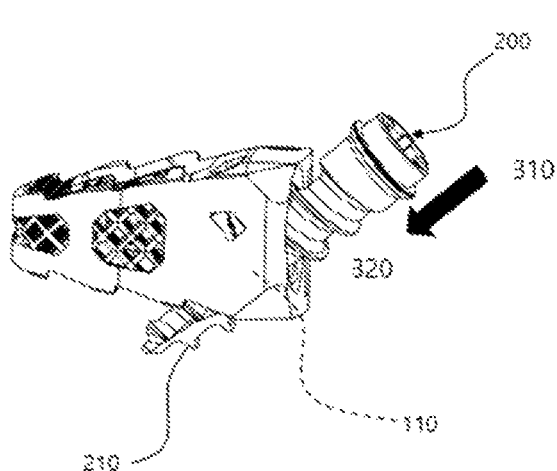

【FIG. 3B】
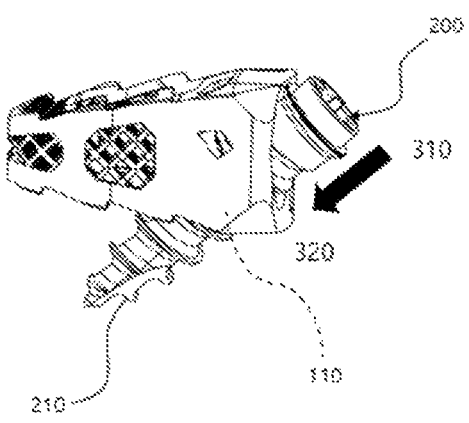

【FIG. 3C】
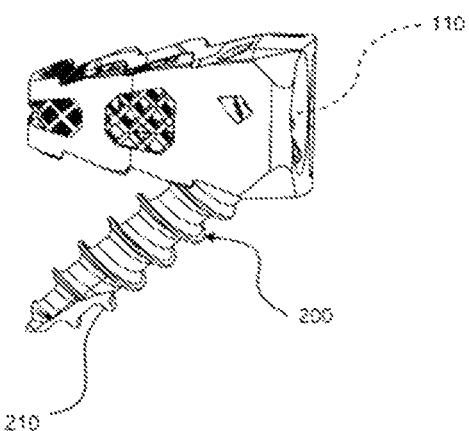

【FIG. 4】
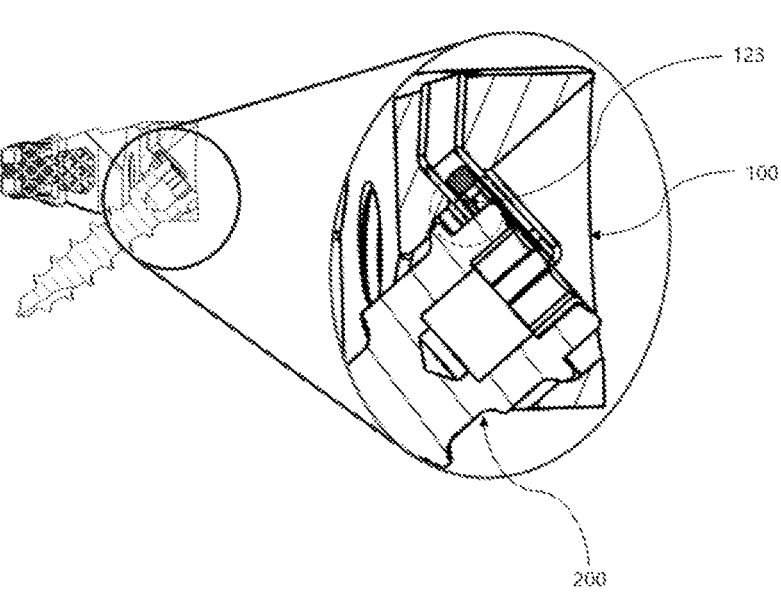

【FIG. 5A】
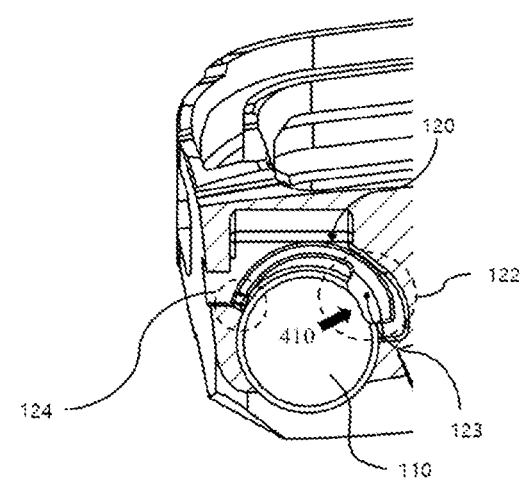

【FIG. 5B】
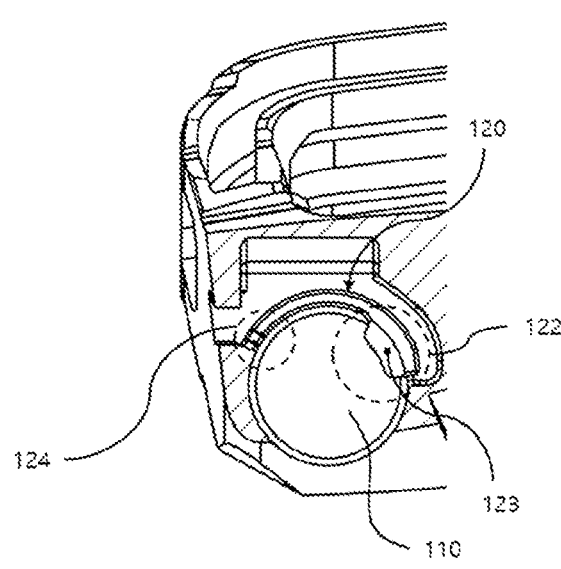

【FIG. 6】
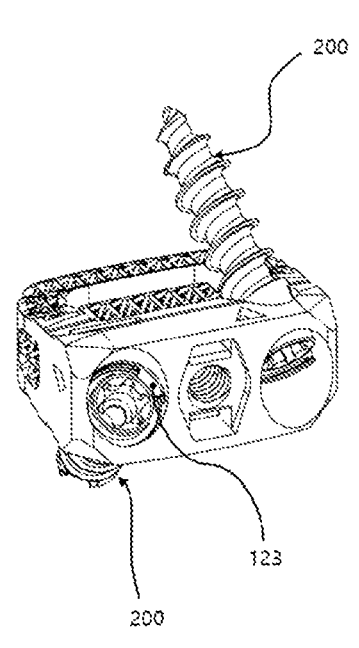

INTERBODY FUSION DEVICE

CROSS REFERENCE TO RELATED APPLICATION

The present application claims priority to Korean Patent Application No. 10-2022-0054779, filed May 3, 2022, the entire contents of which are incorporated herein for all purposes by this reference.

BACKGROUND OF THE INVENTION

Field of the Invention

The present disclosure relates to an interbody fusion device.

Description of the Related Art

Structural problems in the spine, such as anomalies in the alignment or narrowing of the space between vertebral bodies, can develop for a variety of reasons including congenital conditions, degeneration, or accidents. Spine disorders such as spine deformity include malformation of spine, Spinal fractures, herniated intervertebral discs, spinal stenosis, and facet joint hypertrophy.

Typically, the treatment of spine-related conditions includes indirect treatment through physical therapy and direct treatment involving correction and fixation of the spine by attaching a separate fixation device to the damaged vertebrae. For the direct treatment that physically corrects a damaged spine, an interbody fusion device is used, and a fixator such as a screw or an anchor may be used to fix the interbody fusion device.

That is, the interbody fusion device is a medical device that is inserted between the vertebral bodies where a damaged disc is removed and secures the disc space until adjacent vertebrae are fused. At this time, it is necessary to prevent the interbody fusion device inserted between the vertebral bodies from being displaced from its original position. In other words, in order to prevent displacement of the interbody fusion device inserted between the vertebral bodies, a standalone method using fixators such as screws or anchors may be used, as an example.

Yet, when immobilizing the interbody fusion device using a fixator, the fixator inserted into a body is pushed back little by little by continuous movements of the body. The displaced fixator causes various problems including dysphagia which is a sensation that food is stuck in the esophagus, damage to surrounding soft tissues and displacement of the interbody fusion device. Accordingly, there is a need for a locking device to prevent the displacement of fixators.

To prevent displacement of a fixator, the fixator may be fixed using a method in which a C-shape retaining ring having elasticity is coupled to the fixator, and the C-shape retaining ring is caught on the step formed inside an interbody fusion device. However, since this method uses additional accessories, manufacturing costs may increase, and a locked state may be unstable as a locking area changes depending on the angle at which the fixator is installed.

Alternatively, an additional member, for example a locking plate, may be used to prevent a fixator from being dislodged after being inserted. That is, after the fixator is inserted, the fixator is fixed by attaching the member to a hole into which the fixator is inserted or by rotating the member.

In this regard, Korean Patent No. 10-2122716 proposes a method of using a rotary locking part to lock a bone fixation screw. The problem with this method is that the manufacturing cost increases because additional accessories are used, a separate action for locking is additionally required because a rotation state must be changed for locking, and the locked state is unstable due to the fixation problem of the rotary locking part.

In order to solve the above problems, there is an emerging need for a more efficient and stable locking mechanism for an interbody fusion device fixator.

PRIOR ART DOCUMENT

Documents of Related Art

Korean Patent No. 10-2122716

SUMMARY OF THE INVENTION

Technical Problem

Accordingly, the present disclosure has been made keeping in mind the above problems occurring in the related art, and the present disclosure is intended to provide an interbody fusion device that does not contain additional members and ensures stable locking at the time a fixator is inserted.

However, the objectives of the present disclosure are not limited to the objective mentioned above, other objectives not mentioned will become clear to those skilled in the art from the description below.

Technical Solution

In order to achieve the above objective, according to an embodiment of the present disclosure, there is provided an interbody fusion device including: a circular opening into which a fixator is inserted; an elastic band configured to surround at least a portion of the circular opening, and comprising a first distal end including a fixing part protruding from the circular opening to prevent separation of the fixator; and a connection part connected to a second distal end of the elastic band.

The elastic band may be implemented with the same material as the interbody fusion device, and the elastic band and the interbody fusion device may be integral.

The elastic band may be unable to be separated from the interbody fusion device.

The interbody fusion device may be processed through additive manufacturing.

When an insertion of the fixator through the circular opening is completed, the fixing part may return to a protruding state in the circular opening.

The fixing part may block an escape path of the fixator so that the fixator does not depart from an inserted position.

Advantageous Effects

According to an interbody fusion device of the present disclosure, it is possible to provide an efficient locking mechanism for interbody fusion devices since no specially manufactured parts are required to support a fixator.

According to the interbody fusion device of the present disclosure, it is possible to provide an efficient locking mechanism for interbody fusion devices due to a manufacturing method that does not increase manufacturing costs.

According to the interbody fusion device of the present disclosure, it is possible to provide a locking mechanism for interbody fusion devices with improved stability since stable locking can be ensured due to simple structure and manufacturing method.

BRIEF DESCRIPTION OF THE DRAWINGS

The above and other objectives, features, and other advantages of the present disclosure will be more clearly understood from the following detailed description when taken in conjunction with the accompanying drawings, in which:

FIG. 1 is a perspective view of an interbody fusion device according to an embodiment of the present disclosure;

FIG. 2 is an enlarged cross-sectional view showing a circular opening of the interbody fusion device according to the embodiment of the present disclosure;

FIGS. 3A to 3C are side views in which a fixator is inserted into the interbody fusion device through the circular opening:

FIG. 4 is an enlarged cross-sectional view showing a fixing part of an elastic band after the fixator is inserted;

FIG. 5A is an enlarged perspective view of the circular opening at the moment when the elastic band is pressed during the process of inserting the fixator into the interbody fusion device according to the present embodiment;

FIG. 5B is an enlarged perspective view of the circular opening before or after the fixator is inserted into the interbody fusion device according to the present embodiment; and FIG. 6 is a perspective view after the fixator is inserted into the interbody fusion device according to the present embodiment.

DETAILED DESCRIPTION OF THE INVENTION

The present disclosure relates to an interbody fusion device.

More particularly, the present disclosure relates to an interbody fusion device comprising: a circular opening into which a fixator can be inserted; an elastic band that surrounds at least a portion of the circular opening, and comprises a first distal end including a fixing part protruding from the circular opening to prevent separation of the fixator; and a connection part connected to a second distal end of the elastic band. And the elastic band is implemented with the same material as the interbody fusion device, and the elastic band and the interbody fusion device are integral.

Embodiments of the present disclosure will be described in detail with reference to the accompanying drawings. However, since the drawings accompanying this specification illustrate preferred embodiments of the present disclosure and serve to further understand the technical idea of the present disclosure together with the contents of the above description, the present disclosure should not be construed as being limited only to the matters described in the drawings. In addition, in order to clearly describe the present disclosure in the drawings, parts irrelevant to the description are omitted, and similar reference numerals are assigned to similar parts throughout the specification.

Terms used in this specification are for describing the embodiments, and are not intended to limit the present disclosure. In this specification, the singular form includes the plural form unless specifically stated otherwise.

The terms "comprises" and/or "comprising" used herein mean not excluding the presence or addition of one or more other components, steps, operations and/or members other than the mentioned components, steps, operations and/or members. Like reference numerals designate like elements throughout the specification.

The spatially relative terms "below", "beneath", "lower", "above", "upper", etc. may be used to easily describe the relationship between one member or component and another member or component as shown in the drawings. These spatially relative terms should be understood as encompassing different orientations of the member in use or operation in addition to the orientation shown in the drawings. For example, when inverting a member shown in the drawing, a member described as "below" or "beneath" another member may be placed "above" another member. Thus, the exemplary term "below" may include directions of both below and above. Elements may also be oriented in other orientations, and thus the spatially relative terms may be interpreted according to orientation.

Throughout the specification, "planar view" means when a subject part is viewed from above, and "cross-sectional view" means a cross section of a subject part cut vertically when viewed from the side.

Furthermore, throughout the specification, "overlapping" means overlapping up and down in cross section, or all or part of being located in the same area on a plane.

Hereinafter, an embodiment of the present disclosure will be described in detail. However, the present disclosure may be embodied in many different forms and should not be construed as limited to the embodiments set forth herein. The embodiments are provided only to make the disclosure of the invention complete, and to completely inform those skilled in the art of the scope of the invention to which the present disclosure belongs. The present disclosure is only defined by the scope of the claims.

FIG. 1 is a perspective view of an interbody fusion device 100 according to an embodiment of the present disclosure, and FIG. 2 is an enlarged cross-sectional view showing a circular opening 110 of the interbody fusion device according to the embodiment of the present disclosure.

Referring to FIGS. 1 and 2, the interbody fusion device 100 according to the embodiment of the present disclosure may include the circular opening 110, an elastic band 120, a first distal end 122 provided in the elastic band 120, a fixing part 123, a second distal end 124, and a connection part 125. The interbody fusion device 100 according to the embodiment is not limited to the circular opening 110, the elastic band 120, and the connection part 125, and may further include additional components necessary for the operation of the interbody fusion device 100.

In addition, in this embodiment, the terms top (upper) and bottom (lower), front and rear, front, plane, side, and bottom, and outside and inside are used for the convenience of description, and may exist in a form different from the term used in each component depending on the embodiment of the interbody fusion device 100.

The interbody fusion device 100 may include at least one or more circular openings 110. Although in FIGS. 1 and 2, the interbody fusion device 100 is shown as including two circular openings 100, but is not limited thereto, and the interbody fusion device 100 may have only one circular opening 110 or may have three or more circular openings 110. In addition, the circular opening 110 and related descriptions below may be applied to all circular openings 110 provided in the interbody fusion device 100.

The circular opening 110 may be implemented into which a fixator is inserted. At this time, the fixator may be a screw or an anchor, but is not limited thereto. In addition, the circular opening 110 according to this embodiment may include the elastic band 120 to be described below.

The circular opening 110 and the fixator 200 will be described below with reference to FIGS. 3A to 3C.

FIGS. 3A to 3C are views showing step-by-step side views in which the fixator 200 is inserted through the circular opening of the interbody fusion device 100.

FIGS. 3A to 3C show a state in which the fixator 200 is inserted into the interbody fusion device 100 through the circular opening 110. As shown in FIGS. 3A to 3C, a thread 210 provided in the fixator 200 allows the fixator 200 to smoothly move from an outer side 310 to an inner side 320 through rotation within the circular opening 110 so as to be inserted into the interbody fusion device 100. However, the configuration of the fixator 200 is not limited thereto, and the fixator 200 may be of a threadless type or may be an anchor. At this time, the outer side 310 according to this embodiment may mean a direction in which the fixator 200 starts to be inserted, that is, a direction far from the spine, while the inner side 320 may mean a direction in which the insertion of the fixator 200 is completed, that is, a direction closer to the spine.

Referring to FIG. 3C, the insertion of the fixator 200 into the interbody fusion device 100 through the circular opening 110 is completed. As the insertion of the fixator 200 into the interbody fusion device 100 is completed, the interbody fusion device 100 may be fixed to the spine (not shown).

FIG. 4 is an enlarged cross-sectional view showing the fixing part of the elastic band in a state in which the fixator 200 is completely inserted into the interbody fusion device 100 as shown in FIG. 3C.

Referring to FIGS. 1 and 2 again, the elastic band 120 surrounds at least a portion of the circular opening 110, the first distal end 122 includes the fixing part 123 that protrudes from the circular opening 110, and the second distal end 124 is connected to the interbody fusion device 100 by means of the connection part 130. For example, as shown in FIG. 4, the elastic band 120 according to the embodiment may be present on the outermost side of the circular opening 110 so that the fixing part 123 of the elastic band 120 blocks the escape path of the fixator 200 in a state in which the fixator 200 is fully inserted, but is not limited thereto.

For the elastic band 120 according to the embodiment, same material as the interbody fusion device 100, for example, any medical material having elasticity such as titanium alloy (Ti-6Al-4V-ELI) and suitable for additive manufacturing may be used without limitation. In addition, as the interbody fusion device 100 is processed through additive manufacturing, the elastic band 120 may be integrally implemented with the interbody fusion device 100. That is, since the elastic band 120 cannot be separated from the interbody fusion device 100, the fixator 200 may be stably fixed. As the interbody fusion device 100 is implemented in this way, no additional accessories are used to manufacture the elastic band 120 and the fixing part 123, thereby minimizing an increase in manufacturing cost.

FIGS. 5A and 5B are cross-sectional views showing the movement of the elastic band when the fixator is inserted. To be specific, the elastic band 120 may be fixed to the interbody fusion device 100 as the elastic band 120 surrounds at least a portion of the circular opening 110, and the second distal end 124 of the elastic band 120 is integrally manufactured and connected to the interbody fusion device 100 by means of the connection part 130. On the other hand, the first distal end 122 of the elastic band 120 includes the fixing part 123, and the fixing part 123 may move according to whether or not the fixator is inserted along with the movement of the elastic band 120.

The elastic band 120 according to the embodiment is shown as surrounding about half of the circular opening 110, but is not limited thereto, and the elastic band 120 may be implemented in a form surrounding a part or the whole of the circular opening 110.

The movement of the elastic band 120 and the fixing part 123 when the fixator 200 is inserted will be described in more detail with reference to FIGS. 5A and 5B.

Referring to FIG. 5A, when the fixator 200 is inserted through the circular opening 110, the fixing part 123 moves outward from the circular opening 110 by a force 410 applied by the fixator, and exists in a state that does not protrude from the circular opening 110. That is, as the fixing part 123, which exists in the form of protruding from the circular opening 110, is pressed by the force 410 applied by the fixator, the fixing part 123 moves outward from the circular opening 110.

As shown in FIG. 5B, when the insertion of the fixator (not shown) through the circular opening 110 is completed, the fixing part 123 returns to a protruding state in the circular opening 110 by the elastic force of the elastic band 120. Accordingly, the fixing part 123 may block the escape path of the fixator (not shown) so that the fixator does not depart from the inserted position.

Referring to FIGS. 1 to 3C again, displacement of the fixator 200 is prevented by using the elastic force of the elastic band 120 and the fixing part 123 provided thereon according to the present embodiment. In other words, due to the elastic fixing part 123 integrally coupled to interbody fusion device 100, the displacement of the fixator 200 may be effectively prevented, unlike the case in which separately manufactured elastic parts are assembled to the interbody fusion device 100.

Moreover, according to the interbody fusion device 100 of the present embodiment, since the elastic band 120 and the fixing part 123 are integrally manufactured through additive manufacturing, and the interbody fusion device 100, the elastic band 120, and the fixing part 123 are all made of the same material, additional parts and assembly are not required, thereby preventing an increase in production cost.

Furthermore, no additional user action is required to lock the fixator 200 since the displacement of the fixator 200 may be prevented by using the elastic force of the elastic band 120.

In addition, since the fixing part 123 of the elastic band 120 exists in a form protruding from the circular opening 110, a constant fixation area may be provided regardless of the angle at which the fixator 200 is inserted, thereby providing a stable locking effect.

In addition, in case unlocking the fixator 200 is necessary, it is possible to unlock the fixator 200 and remove the fixator 200 from the interbody fusion device 100 without using an additional tool other than a dedicated screwdriver for the fixator 200.

FIG. 6 is a perspective view showing a state in which the fixator 200 is fixed by the fixing part 123 while the fixator 200 is coupled to the interbody fusion device 100 according to the present embodiment.

Referring to FIG. 6, as the fixing part 123 blocks the escape path of the fixator 200, it is possible to prevent the fixator 200 from being separated after being inserted into the spine. When two or more fixators 200 are inserted, the circular openings of the interbody fusion device 100 may be made in different directions as shown in FIG. 6 so that the fixators 200 are inserted at different angles, but the present disclosure is not limited thereto.

Meanwhile, in the embodiment of the present disclosure, the interbody fusion device 100 may include a cavity part formed in a shape penetrating the central portion thereof in the vertical direction. The bone may be regenerated by itself through the cavity part, or a bone fusion material may be accommodated in the cavity part to facilitate bone integration, thereby increasing the fixing force of the interbody fusion device of the present disclosure. The bone fusion material may include, for example, autologous bone, allograft bone, bone substitute, osteoinductive agent, and/or bone cement, but is not limited thereto.

In conclusion, the interbody fusion device 100 according to the present embodiment may ensure a stable locked state while boasting an uncomplicated structure and a simple manufacturing method.

EXPLANATION OF REFERENCE NUMERALS

100: an interbody fusion device
110: a circular opening
120: an elastic band
122: a first distal end
123: a fixing part
124: a second distal end
125: a connection part
200: a fixator
210: a thread
310: an outer side
320: an inner side
410: a force applied by the fixator

What is claimed is:

1. An interbody fusion device, comprising:
a circular opening into which a fixator is inserted;
an elastic band configured to annularly surround at least a portion of an interior of the circular opening in a ring shape, and comprising a first distal end including a fixing part protruding outwardly from the interior sidewall of the circular opening to prevent separation of the fixator; and
a connection part connected to a second distal end of the elastic band,
wherein the elastic band is implemented with the same material as the interbody fusion device;
wherein the elastic band is disposed on an outermost side of the circular opening;

wherein, when the fixator is inserted through the circular opening, the fixing part exists in a state that does not protrude from the circular opening;
wherein when an insertion of the fixator through the circular opening is completed, the fixing part returns to a protruding state in the circular opening; and
wherein the elastic band and the interbody fusion device are integral.

2. The interbody fusion device of claim 1, wherein the elastic band is unable to be separated from the interbody fusion device.

3. The interbody fusion device of claim 1, wherein the interbody fusion device is processed through additive manufacturing.

4. The interbody fusion device of claim 1, wherein the fixing part blocks an escape path of the fixator so that the fixator does not depart from an inserted position.

5. The interbody fusion device of claim 1, wherein the elastic band is entirely disposed on an outermost side of the circular opening.

6. The interbody fusion device of claim 1, wherein the connection part is positioned within the circular opening.

7. An interbody fusion device, comprising:
a circular opening into which a fixator is inserted;
an elastic band positioned along an interior sidewall of the circular opening and entirely within the circular opening,
wherein the elastic band includes a first distal end having a fixing part that protrudes outwardly from the interior sidewall of the circular opening to prevent separation of the fixator, and a second distal end connected to the interior sidewall of the circular opening via a connection part,
wherein the elastic band is implemented with the same material as the interbody fusion device,
wherein the elastic band is disposed on an outermost side of the circular opening;
wherein, when the fixator is inserted through the circular opening, the fixing part exists in a state that does not protrude from the circular opening;
wherein when an insertion of the fixator through the circular opening is completed, the fixing part returns to a protruding state in the circular opening; and
wherein the elastic band and the interbody fusion device are integral.

\* \* \* \* \*